(12) United States Patent
Buynak et al.

(10) Patent No.: US 7,022,691 B2
(45) Date of Patent: Apr. 4, 2006

(54) INHIBITORS OF SERINE AND METALLO-β-LACTAMASES

(75) Inventors: John D. Buynak, 10842 Hayfield Dr., Dallas, TX (US) 75238; Hansong Chen, 6142 Fisher Rd., apt 142-1, Dallas, TX (US) 75214

(73) Assignees: John D. Buynak, Dallas, TX (US); Hansong Chen, Germantown, MD (US)

( * ) Notice: Subject to any disclaimer, the term of this patent is extended or adjusted under 35 U.S.C. 154(b) by 34 days.

(21) Appl. No.: 10/407,844

(22) Filed: Apr. 4, 2003

(65) Prior Publication Data

US 2003/0216372 A1 Nov. 20, 2003

Related U.S. Application Data

(60) Provisional application No. 60/370,499, filed on Apr. 4, 2002.

(51) Int. Cl.
*C07D 499/87* (2006.01)
*C07D 499/861* (2006.01)
*A61K 31/43* (2006.01)
*A61K 31/431* (2006.01)
*A61P 31/04* (2006.01)

(52) U.S. Cl. ................................ 514/208; 540/310
(58) Field of Classification Search ................ 514/208; 540/310
See application file for complete search history.

(56) References Cited

U.S. PATENT DOCUMENTS

| | | | |
|---|---|---|---|
| 4,053,468 A | 10/1977 | Holden | 544/30 |
| 4,356,174 A | 10/1982 | Barth | 424/114 |
| 4,512,999 A | 4/1985 | Adam-Molina et al. | 514/192 |
| 4,559,157 A | 12/1985 | Smith et al. | 252/90 |
| 4,608,392 A | 8/1986 | Jacquet et al. | 514/844 |
| 4,820,508 A | 4/1989 | Wortzman | 424/59 |

(Continued)

FOREIGN PATENT DOCUMENTS

DE    2708219    9/1977

(Continued)

OTHER PUBLICATIONS

ABD El-Nabi, H. A., "Novel Heterocycles: A convenient Synthesis of Pyrrolo [2,3-d]pyrazole; Cycloaddition reaction of N-aryl(methyl)pyrrol-2,3-Diones to diazomethane and olefins", *Tetrahedron*, 53(5), (Feb. 1997), 1813-1822.

(Continued)

*Primary Examiner*—Mark L. Berch

(57) ABSTRACT

Compounds of formula (I):

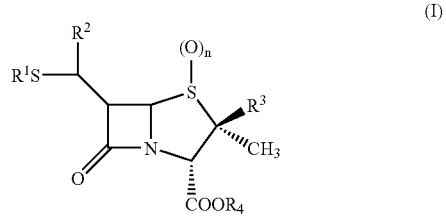

wherein $R^1$, $R^2$, $R^3$, $R^4$ and n have any of the values defined in the specification, and their pharmaceutically acceptable salts, are useful for inhibiting simultaneously serine and metallo-β-lactamase enzymes, for enhancing the activity of β-lactam antibiotics, and for treating β-lactam resistant bacterial infections in a mammal. The invention also provides pharmaceutical compositions, processes for preparing compounds of formula I, and novel intermediates useful for the synthesis of compounds of formula I.

4 Claims, 6 Drawing Sheets

U.S. PATENT DOCUMENTS

| | | | | |
|---|---|---|---|---|
| 4,826,833 | A | 5/1989 | Chen | 514/192 |
| 4,861,768 | A | 8/1989 | Torii et al. | 514/195 |
| 4,912,213 | A | 3/1990 | Taniguchi et al. | 540/310 |
| 4,938,949 | A | 7/1990 | Borch et al. | 424/10 |
| 4,992,478 | A | 2/1991 | Geria | 514/782 |
| 5,597,817 | A | 1/1997 | Buynak et al. | 514/200 |
| 5,629,306 | A | 5/1997 | Buynak et al. | 514/206 |
| 5,637,579 | A | 6/1997 | Hubschwerlen et al. | 514/192 |
| 5,681,563 | A | 10/1997 | Buynak et al. | 424/114 |
| 5,760,027 | A | 6/1998 | Buynak et al. | 514/200 |
| 6,156,745 | A | 12/2000 | Buynak et al. | 514/192 |
| 6,391,855 | B1 | 5/2002 | Blaschuk et al. | 514/17 |

FOREIGN PATENT DOCUMENTS

| | | |
|---|---|---|
| EP | 0041047 | 12/1981 |
| EP | 0050805 | 5/1982 |
| EP | 0150984 | 8/1985 |
| EP | 0170192 | 2/1986 |
| EP | 0367606 | 5/1990 |
| EP | 0043546 | 1/1992 |
| GB | 2043639 | 10/1980 |
| JP | 55-136288 | 10/1980 |
| JP | 57-99590 | 6/1982 |
| JP | 58-59990 | 4/1983 |
| JP | 61-109791 | 5/1986 |
| JP | 62-198687 | 9/1987 |
| JP | 64-66189 | 3/1989 |
| JP | 7-82273 | 3/1995 |
| WO | WO-96/17849 | 6/1996 |
| WO | WO-98/24793 | 6/1998 |
| WO | WO-00/63213 | 10/2000 |
| WO | WO-03/020732 | 3/2003 |

OTHER PUBLICATIONS

Adam, Solange, "Synthesis of Methylene (R)-6-acetonylidene-3-methyl-7-oxo-4-thia-1-azabicyclo [3.2.0] hept-2-ene-carboxylate pivalate", *Heterocycles*, 22(7), Columbus, Ohio, U.S., (1984), 1509-1512.

Arisawa, M., et al., "6-Acetylmethylenepenicillanic Acid (Ro 15-1903), A Potent B-Lactamasae Inhibitor. I. Inhibition of Chromosomally and R-Factor-Mediated B-Lactamases", *The Journal of Antibiotics*, 35(11), (Nov. 1982), 1578-1583.

Beharry, Zanna, et al., "Penicillin-Derived Inhibitors of the Class A B-Lactamase from *Bacillus Anthracis*", ICAAC Poster # C1-679, Chicago, IL, (2003), 6 pgs.

Bennett, I. S., et al., "6-(Substituted Methylene)Penems, Potent Broad Spectrum Inhibitors of Bacterial B-Lactamse. V. Chiral 1,2,3-Triazolyl Derivatives", *The Journal of Antibiotics*, 44(9), (Sep. 1991), 969-978.

Billups, W. E., et al., "Generation of Simple Methylenecyclopropenes as Reactive Intermediates", *Tetrahedron*, 37, (1981), 3215-3220.

Bitha, P., et al., "6-(1-Hydroxyalkyl)Penam Sulfone Derivatives as Inhibitors of Class A and Class C .beta.-Lactamases I", *Bioorganic & Medicinal Letters*, 9(7), (1999), 991-996.

Bitha, P., et al., "6-(1-Hydroxyalkyl)Penam Sulfone Derivatives as Inhibitors of Class A and Class C .beta.-Lactamases II", *Bioorganic & Medicinal Chemistry Letters*, 9(7), (1999), 997-1002.

Black, Jennifer, et al., "Detection of Plasmid-Mediated AmpC B-Lactamases (pAmpCs) in Disk Tests Based on B-Lactamase Inhibitors (BLIs) Ro 48-1220 (RO) and LN-2-128 (LN)", *43rd ICCAC Poster # D-258*, (2003), 6 pgs.

Blacklock, Thomas J., et al., "A Versatile Synthesis of 1,1-Dioxo 7-Substituted Cephems: Preparation of the Human Leukocyte Elastase (HLE) Inhibitor 1,1-Dioxo-trans-7-methoxycephalosporanic Acid tert-Butyl Ester", *J. Org. Chem.*, 54, (1989), 3907-3913.

Brenner, D. G., et al., "6-(Methoxymethylene)penicillanic Acid: Inactivator of RTEM B-Lactamse from *Escherichia coli*", *Biochemistry*, 23(24), (Nov. 20, 1984), 5839-5846.

Buynak, John D., et al., "7-Alkylidenecephalosporin Esters as Inhibitors of Human Leukocyte Elastase", *J. Med. Chem.*, 40, (1997), pp. 3423-3433.

Buynak, John D., et al., "A Convenient Method for the Production of 6-Oxopenicillinates and 7-Oxocephalosporinates", *Tetrahedron Letters*, 39, (1998), 4945-4946.

Buynak, John D., et al., "a-Alkylidene B-Lactams. 2. A Formal Synthesis of (+)-Carpetimycin A", *J. Org. Chem.*, 51, (1986), 1571-1574.

Buynak, John D., et al., "Catalytic Approaches to the Synthesis of B-Lactamase Inhibitors", *Tetrahedron*, 56, (2000), 5709-5718.

Buynak, J. D., "Cephalosporin-Derived Inhibitors of beta-Lactamase. Part 4: The C3 Substituent", *Bioorganic & Medicinal Chemistry Letters*, 12, Online Apr. 24, 2002, 1663-1666.

Buynak, J. D., "Coupling Reactions of Cephalosporin Sulfones: A Stable 3-Stannylated Cephem", *Org. Lett. 2001*, 3(19), (Aug. 30, 2001), 2953-2956.

Buynak, John D., et al., "Penicillin-Derived Inhibitors that Simultaneously Target Both Metallo- and Serine-B-Lactamases", *Bioorganic and Medicinal Chemistry Letters*, (Article in Press, available online), (Jan. 22, 2004), 6 pgs.

Buynak, John D., et al., "Reactions of (Silylamino) phosphines with Epoxides and Episulfides", *J. Org. Chem.*, 49, (1984), 1828-1830.

Buynak, John D., et al., "Stille Coupling Approaches to the Stereospecific Synthesis of 7-[(E)-Alkylidene] cephalosporins", *Tetrahedron Letters*, 40, (1999), 1281-1284.

Buynak, John D., "Synthesis and biological activity of 7-alkylidenecephems", *J. Med. Chem.*, 38, (1995), 1022-1034.

Buynak, John D., et al., "Synthesis and mechanistic evaluation of 7-vinylidenecephem sulfones as B-lactamase inhibitors", *J. of Am. Chem. Soc.*, 116, (1994), 10955-10965.

Buynak, John D., et al., "Synthesis and Reactivity of Sulfur and Silyl Substituted a-Alkylidene-B-Lactams", *Tetrahedron Letters*, 26, (1985), 5001-5004.

Buynak, J. D., et al., "Synthesis of 6-vinylidenepenams", *The Journal of Organic Chemistry*, 58 (6), (Mar. 12, 1993), 1325-1335.

Buynak, John D., et al., "Synthesis of the First 2', 6 Bridged Penams", *J. Am. Chem. Soc.*, 120, (1998), 6846-6847.

Buynak, John D., et al., "The Addition of Chlorosulphonyl Isocyanate to an Allenyl Acetate. The Preparation of a Versatile Intermediate for Antibiotic Synthesis", *J. Chem. Soc., Chem. Commun.*, (1984), 948-949.

Buynak, John D., et al., "The Preparation and Use of Metallo-6-vinylidene Penams", *J. Chem. Soc., Chem. Commun.*, (1990), 294-296.

Buynak, John D., et al., "The Preparation of the First a-Vinylidene-B-lactams", *J. Chem. Soc., Chem. Commun.*, (1987), 735-737.

Buynak, John D., "The Preparation of the First a-Vinylidenepenams", *Tetrahedron Letters*, 29, (1988),5053-5056.

Buynak, J. D., "The Synthesis and Evaluation of 2-Substituted-7-(alkylidene)cephalosporin Sulfones as beta-Lactamase Inhibitors", *Bioorganic & Medicinal Chemistry Letters*, 10, (2000),847-851.

Buynak, J. D., "The Synthesis and Evaluation of 3-Substituted-7-(alkylidene)cephalosporin Sulfones as beta-Lactamase Inhibitors", *Bioorganic & Medicinal Chemistry Letters*, 10, (2000),853-857.

Buynak, John D., "The Synthesis and Evaluation of 6-alkylidene-2'beta-substituted penam sulfones as beta-lactamase inhibitors", *Bioorg. Med. Chem. Lett.*, 9, (Jul. 9, 1999),1997-2002.

Buynak, J. D., et al., "The Synthesis and Lactamase Inhibitory Activity of 6-(Carboxymethylene) Pencillins and 7-(Carboxymethylene)Cephalosporins", *Bioorganic & Medicinal Chemistry Letters*, 5 (14), (1995),1513-1518.

Chen, Y. L., et al., "Synthesis of a Potent B-Lactamase Inhibitor-1,1-Dioxo-6-(2-Pyridyl)Methylenepenicillanic Acid and its Reaction with Sodium methoxide", *Tetrahedron Letters*, 27 (30), (1986),3449-3452.

Crichlow, G. V., "Inhibition of Class C beta-Lactamases: Structure of a Reaction Intermediate with a Cephem Sulfone", *Biochemistry*, 40, (2001),6233-6239.

De Meester, Patrice, et al., "3-[(Z)-p-Chlorophenylthio-(E)-trimethylsilylmethylidene]-1,4-dimethyl-4-trimethylsilylazetidin-2-one: an a-Alkylidene-B-lactam", *Acta Cryst., C42*, (1986), 1260-1262

Dininno, Frank, et al., "Aldol Condensations of Regiospecific Penicillanate and Cephalosporanate Enolates. Hydroxyethylation at C-6 and C-7", *J. Org. Chem.*, 42, (1977),2960-2965.

Farina, Vittorio, et al., "A General Route to 3-Functionalized 3-Norcephalosporins", *J. Org. Chem.*, 54, (1989), 4962-4966.

Gutsche, C. D., "The Chemistry of Carbonyl Compounds", *Prentice-Hall, Englewood Cliffs, NY*, 46-47.

Haebich, D., et al., "Abstract of Inhibitors of .beta. -lactamases. 2. Synthesis of 6-sulfonylmethylene-, 6-sulfinylmethylene- and spiropyrazoline- penicillanic acids", CA 105: 114785.

Hagiwara, D., et al., "An Efficient Synthesis of 6-Oxopenicillanic and 7-Oxocephalosporanic Acid Derivatives", *Journal of the Chemical Society Chemical Communications*, 11, (Jun. 1, 1982),578-579.

Kant, J., et al., "Diastereoselective Addition of Grignard Reagents to Azetidine-2,3dione: Synthesis of Novel Taxol Analogues", *Tetrahedron Letters*, 37 (36), (Sep. 2, 1996), 6495-6498.

Kollenz, G., et al., "Reactions of Cyclic Oxalyl Compounds—38. New Isoindigoide Dyes from Heterocyclic 2,3-Diones—Synthesis and Thermal Rearrangement", *Tetrahedron*, 52(15), (Apr. 1996),5427-5440.

Mak, Ching-Pong, et al., "Chemicl Studies on the Transformation of Penicillins I. Synthesis of Cyclic Disulfides and Thiosulfinates Related to Asparagusic Acid", *Heterocycles*, 27(2), Columbus, Ohio, U.S.,(1988),331-337.

Martin, Micahel G., et al., "Epoxides as Alkene Protecting Groups. A Mild and Efficient Deoxygenation", *Tetrahedron Letters*, 25 (3), (1984),pp. 251-254.

Miyashita, Kazuyuki, et al., "Design, Synthesis, and Evaluation of a Potent Mechanism-Based Inhibitor for the TEM B-Lactamase with Implications for the Enzyme Mechanism", *J. Am. Chem. Soc.*, 117, (1995),11055-11059.

Murata, Y., et al., Abstract of "Acute, Subacute, and Chronic Parenteral Toxicities of disodium alpha.-sulfobenzylpencillin (Sulfocillin) in Mice, Dogs, and Rats", CA 76:147.

Palomo, C., et al., "New Synthesis of a-Amino Acid N-Carboxy Anhydrides through Baeyer-Villiger Oxidation of a-keto B-Lactams", *The Journal of Organic Chemistry*, 59 (11), (Jun. 3, 1994), 3123-3130.

Roberts, John D., et al., "Basic Principles of Organic Chemistry", *Benjamin, NY*, (1964),405, 537.

Siriwardane, Upali, et al., "1,1,3'-Trimethyl-3'-(trimethylsilyl)perhydroazetidino[1,2-c][1,3]oxazine-5-spiro-2'-oxiran-6-one, a Novel B-Lactam", *Acta Cryst., C45*, (1989),531-533.

Siriwardane, Upali, et al., "4-Benzyl-3-(ethenylidene) azetidin-2-one: the First a-Vinylidene-B-lactam", *Acta Cryst., C43*, (1987),2242-2243.

Siriwardane, Upali, et al., "4-Methyl-3-{(Z)-methyl[(E)-dimethyl(phenyl)silyl]methylidene}azetidin-2-one: an a-Alkylidene-B-lactam", *Acta Cryst., C44*, (1988),391-393.

Van Der Veen, J. M., et al., "Synthesis of Azetidine-2,3-diones (a-Keto B-Lactams) via 3-(Phenylthio)-2-azetidinones", *The Journal of Organic Chemistry*, 54 (24), (Nov. 24, 1989),5758-5762.

Volkmann, R. A., et al., "Efficient Preparation of 6,6-Dihalopenicillanic Acids. Synthesis of Penicillanic Acid S,S-Dioxide (Sulbactam)", *J. Org. Chem.*, 47, (1982),3344-3345.

INHIBITORS OF SERINE AND METALLO-β-LACTAMASES

CROSS-REFERENCE TO RELATED APPLICATION

This application claims benefit under 35 U.S.C. § 119(e) of U.S. provisional application Ser. No. 60/370,499, filed Apr. 4, 2002, which application is incorporated herein by reference.

BACKGROUND OF THE INVENTION

The most important mechanism of microbial resistance to β-lactam antibiotics is the bacterial production of β-lactamases, enzymes that hydrolytically destroy β-lactam antibiotics, such as penicillins and cephalosporins. This type of resistance can be transferred horizontally by plasmids that are capable of rapidly spreading the resistance, not only to other members of the same strain, but even to other species. Due to such rapid gene transfer, a patient can become infected with different organisms, each possessing the same β-lactamase.

β-lactamase enzymes have been organized into four molecular classes: A, B, C and D based on amino acid sequence. Class A, includes RTEM and the β-lactamase of *Staphylococcus aureus*, class C, includes the lactamase derived from P99 *Enterobacter cloacae*, and class D are serine hydrolases. Class A enzymes have a molecular weight of about 29 kDa and preferentially hydrolyze penicillins. The class B lactamases are metalloenzymes and have a broader substrate profile than the proteins in the other classes. Class C enzymes include the chromosomal cephalosporinases of gram-negative bacteria and have molecular weights of approximately 39 kDa. The recently recognized class D enzymes exhibit a unique substrate profile that differs significantly from the profile of both class A and class C enzymes.

One strategy for overcoming this rapidly evolving bacterial resistance is the synthesis and administration of β-lactamase inhibitors. Frequently, β-lactamase inhibitors do not possess antibiotic activity themselves and are thus administered together with an antibiotic. One example of such a synergistic mixture is "AUGMENTIN" (a registered trademark of Smithkline Beecham Inc), which contains the antibiotic amoxicillin and the β-lactamase inhibitor, clavulanic acid.

Unfortunately, current commercial inhibitors target only class A β-lactamases, which have historically been the most clinically relevant. Recently, however, there has been an increase in the number of infections possessing class B, C, and D β-lactamases. In fact, some microorganisms produce both class B and class A enzymes, potentially making it possible for the metallolactamases to actually protect the serine enzymes. Useful inhibitors of class B, C, and D enzymes are, at present, not available clinically. In particular, inhibitors which solely target class B may not be commercially viable, since the relatively low current rate of metallolactamase-mediated infections will not justify the considerable cost of development.

SUMMARY OF THE INVENTION

The present invention provides unique penicillin derivatives that are simultaneously potent inhibitors of both the metallo-β-lactmases as well as one or more of the serine-β-lactamases. Such compounds have commercial and humanitarian significance. Accordingly, the invention provides a compound of formula (I):

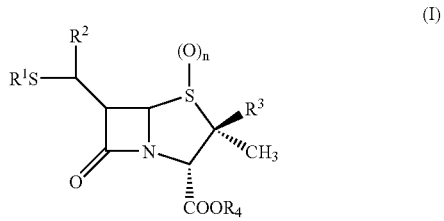

wherein $R^1$ is hydrogen, $(C_1-C_{10})$alkyl, $(C_3-C_8)$cycloalkyl, $(C_2-C_{10})$alkenyl, $(C_2-C_{10})$alkynyl, aryl, arylalkyl, $(C_1-C_{10})$alkanoyl (especially including acetyl), alkoxycarbonyl, heteroaryl, oxazolidinyl, isoxazolidinyl, morpholinyl, heteroarylcarbonyl, alkanoyloxy, or alkoxy;

$R^2$ is hydrogen, carboxy, $(C_1-C_{10})$alkyl, $(C_3-C_8)$cycloalkyl, $(C_2-C_{10})$ alkenyl, $(C_1-C_{10})$alkanoyl, $(C_2-C_{10})$ alkynyl, alkoxycarbonyl, aryl, arylalkyl, heteroaryl, oxazolinyl, isoazolidinyl, morpholinyl, heteroarylcarbonyl, alkanoyloxy, or alkoxy;

$R^3$ is hydrogen, carboxy, $(C_1-C_{10})$alkyl (especially including methyl), $(C_2-C_{10})$alkenyl, $(C_2-C_{10})$alkynyl, $(C_1-C_{10})$alkanoyl, $(C_3-C_8)$cycloalkyl, aryl, arylakyl, heteroaryl, alkoxycarbonyl oxazolinyl, isoazolidinyl, morpholinyl, heteroarylcarbonyl, alkanoyloxy, alkoxy, or $—CH_2R_a$ wherein $R_a$ is halo, cyano, cyanato, $—OR_b$, $—NR_cR_d$, azido, $—SR_e$, $O—CO—R_f$, aryl, heteroaryl (especially including triazolyl and imidazoyl), $(C_3-C_8)$cycloalkyl, oxazolinyl, isoazolidinyl, morpholinyl, heteroarylcarbonyl, alkanoyloxy, or alkoxy;

$R^4$ is hydrogen, carboxy, $(C_1-C_{10})$alkyl, $(C_3-C_8)$cycloalkyl, $(C_2-C_{10})$alkenyl, $(C_2-C_{10})$alkynyl, $(C_1-C_{10})$alkanoyl, alkoxycarbonyl, aryl, heteroaryl, arylalkyl, oxazolinyl, isoazolidinyl, morpholinyl, heteroarylcarbonyl, alkanoyloxy, or alkoxy;

n is 0, 1, or 2;

$R_b$ is hydrogen, $(C_1-C_{10})$alkyl, $(C_3-C_8)$cycloalkyl, $(C_2-C_{10})$alkenyl, $(C_2-C_{10})$alkynyl, $—C(=O)N(R_f)_2$, aryl, heteroaryl, arylcarbonyl, heteroarylcarbonyl, or $(C_1-C_{10})$ alkanoyl, wherein each $R_f$ is independently hydrogen, $(C_1-C_{10})$alkyl, aryl, benzyl, phenethyl, or heteroaryl;

each $R_c$ or $R_d$ is independently hydrogen, $(C_1-C_{10})$alkyl, $(C_3-C_8)$cycloalkyl, $(C_2-C_{10})$alkenyl, $(C_2-C_{10})$alkynyl, $(C_1-C_{10})$alkanoyl, $—C(=O)N(R_g)_2$, aryl, benzyl, phenethyl, heteroaryl oxazolidinyl, isoxazolidinyl, or morpholinyl, wherein each $R_f$ is independently hydrogen, $(C_1-C_{10})$ alkyl, aryl, benzyl, phenethyl, heteroaryl, $NH_2$, or $NR_cR_d$; or $R_c$ and $R_d$ together with the nitrogen to which they are attached are triazolyl, imidazolyl, oxazolidinyl, isoxazolidinyl, pyrrolyl, morpholino, piperidino, pyrrolidino, pyrazolyl, indolyl, or tetrazolyl; and $R_e$ is hydrogen, $(C_1-C_{10})$alkyl, $(C_3-C_8)$cycloalkyl, $(C_2-C_{10})$alkenyl, $(C_2-C_{10})$alkynyl, cyano, aryl, benzyl, phenethyl, heteroaryl, oxazolidinyl, isoxazolidinyl, or morpholinyl;

wherein any $(C_1-C_{10})$alkyl, $(C_3-C_8)$cycloalkyl, $(C_2-C_{10})$ alkenyl, $(C_2-C_{10})$alkynyl, $(C_1-C_{10})$alkanoyl, aryl, benzyl, phenethyl, heteroaryl, arylcarbonyl, heteroarylcarbonyl, oxazolidinyl, isoxazolidinyl, or morpholinyl of $R^1–R^4$, $R_a–R_e$, or $R_f–R_g$, may optionally be substituted with 1, 2, or 3 Z; and each Z is independently halo, nitro, cyano, hydroxy, ($C_1$–$C_{10}$)alkyl, ($C_3$–$C_8$)cycloalkyl, ($C_1$–$C_{10}$)alkoxy, ($C_1$–$C_{10}$)alkanoyl, ($C_2$–$C_{10}$)alkanoyloxy, trifluoromethyl, aryl, aryloxy, or heteroaryl;

or a pharmaceutically acceptable salt thereof.

A preferred structure of the compound of the formula (I) has the relative stereochemistry of the formula:

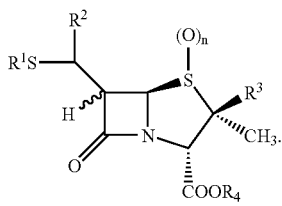

DETAILED DESCRIPTION OF THE INVENTION

Figure 1:
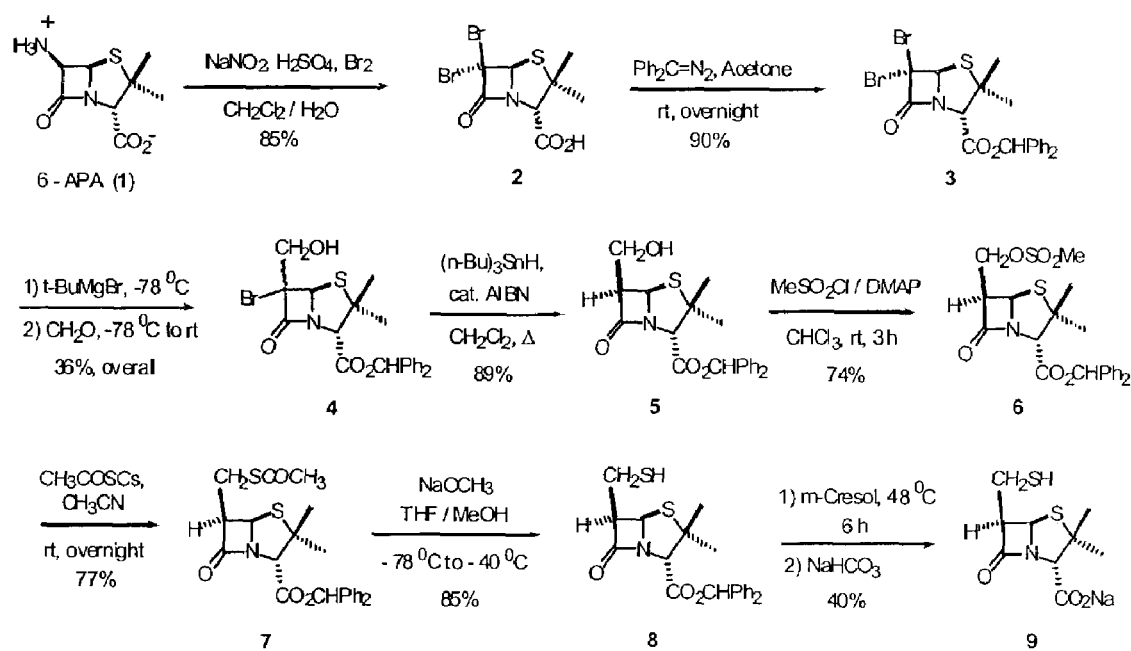
FIG. 1 illustrates the preparation of compounds of the invention.

The following definitions are used, unless otherwise described: halo is fluoro, chloro, bromo, or iodo. Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein each X is absent or is H, O, ($C_1$–$C_4$)alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

It will be appreciated by those skilled in the art that compounds of the invention having one or more chiral centers may exist and be isolated as optically active and racemic forms. Some compounds may exhibit polymorphism. It is to be understood that the present invention encompasses any racemic, optically-active, polymorphic, or stereoisomeric form, or mixtures thereof, of a compound of the invention, that possesses the useful properties described herein, it being well known in the art how to prepare optically active forms (for example, by resolution of the racemic form by recrystallization techniques, by synthesis, from optically-active starting materials, by chiral synthesis, or by chromatographic separation using a chiral stationary phase) and how to determine β-lactamase inhibitory activity using the tests described herein, or using other tests which are well known in the art. Preferably, the absolute stereochemistry of compounds of the invention is that shown in formula I.

Specific and preferred values listed below for radicals, substituents, and ranges, are for illustration only and they do not exclude other defined values or other values within defined ranges for the radicals and substituents.

Specifically, ($C_1$–$C_{10}$)alkyl can be methyl, ethyl, propyl, isopropyl, butyl, iso-butyl, sec-butyl, pentyl, 3-pentyl, hexyl, heptyl, octyl, nonyl or decyl; ($C_3$–$C_8$)cycloalkyl can be cyclopropyl, cyclobutyl, cyclopentyl, cyclohexyl, cycloheptyl, or cyclooctyl; ($C_1$–$C_{10}$)alkoxy can be methoxy, ethoxy, propoxy, isopropoxy, butoxy, iso-butoxy, sec-butoxy, pentoxy, 3-pentoxy, hexyloxy, heptyloxy, octyloxy, nonyloxy, or decyloxy; ($C_2$–$C_{10}$)alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, or 9-decenyl; ($C_2$–$C_{10}$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 2-heptynyl, 3-heptynyl, 4-heptynyl, 5-heptynyl, 6-heptynyl, 1-octynyl, 2-octynyl, 3-octynyl, 4-octynyl, 5-octynyl, 6-octynyl, 7-octynyl, 1-nonylyl, 2-nonynyl, 3-nonynyl, 4-nonynyl, 5-nonynyl, 6-nonynyl, 7-nonynyl, 8-nonynyl, 1-decynyl, 2-decynyl, 3-decynyl, 4-decynyl, 5-decynyl, 6-decynyl, 7-decynyl, 8-decynyl, or 9-decynyl; ($C_1$–$C_{10}$)alkanoyl can be acetyl, propanoyl, butanoyl, isobutanoyl, pentanoyl, hexanoyl, heptanoyl, octanoyl, nonanoyl, or decanoyl; and ($C_2$–$C_{10}$)alkanoyloxy can be acetoxy, propanoyloxy, butanoyloxy, isobutanoyloxy, pentanoyloxy, hexanoyloxy, heptanoyloxy, octanoyloxy, nonanoyloxy, or decanoyloxy. Specifically, "aryl" can be phenyl, indenyl, or naphthyl. Specifically, "heteroaryl" can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), thiadiazolyl, thiatriazolyl, oxadiazolyl, or quinolyl (or its N-oxide). More specifically, "heteroaryl" can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide). More specifically, heteroaryl can be pyridyl.

Specifically, $R^3$ can be methyl, ethyl, propyl, isopropyl, butyl, tert-butyl, pentyl cyclopropyl, cyclopentyl, cyclohexyl, phenyl, toluoyl, anisoyl, mesityl, xylyl, or pyridinyl. More specifically, $R^3$ can be —$CH_2R_a$; $R_a$ is halo, cyano, cyanato, —$OR_b$, —$NR_cR_d$, azido, or —$SR_e$. More specifically, $R^3$ can be triazolylmethyl, imidazoylmethyl, acetoxymethyl, phenylacetoxymethyl, phenoxyacetoxymethyl, chloroacetoxymethyl, pyridylacetoxymethyl, triazolylacetoxymethyl, imidazolylacetoxymethyl, tetrazolylthioacetoxymethyl, or tetrazolylthioacetoxymethyl optionally substituted on the tetrazol ring with ($C_1$–$C_6$)alkyl, or aryl.

Another specific value for $R^3$ is triazoylmethyl, imidazoylmethyl, carbamoyloxymethyl, acetoxymethyl, chloroacetoxymethyl, formyloxymethyl, phenylacetoxymethyl, (1-methyl-i H-tetrazol-5-ylthio)acetoxymethyl, (3,4-dihydroxyphenyl)acetoxymethyl, 3,4-di(4-methoxybenzyloxy) phenylacetoxymethyl, chloromethyl, formyl, or 2-cyanovinyl.

A preferred value for $R^1$, $R^2$, and $R^4$ is hydrogen; and for $R^3$ is methyl.

A preferred group of compounds correspond to sodium, potassium, or lithium salts of compounds of formula I wherein $R^4$ is H;

Another preferred value for $R^2$ is methyl.

Another preferred value for $R^2$ is benzyl ($PhCH_2$).

Another prefered value for $R^2$ is pyridyl (e.g. 2-pyridyl).

Another preferred group of compounds are compounds of formula I wherein $R^3$ is $-CH_2OR_b$, or a pharmaceutically acceptable salt thereof.

Another preferred group of compounds are compounds of formula I wherein $R^3$ is $-CH_2OR_b$, and $R_b$ is $C_2$-alkanoyl, optionally substituted with halo, nitro, cyano, hydroxy, $(C_3-C_8)$cycloalkyl, $(C_1-C_{10})$alkoxy, $(C_1-C_{10})$alkanoyl, $(C_2-C_{10})$alkanoyloxy, trifluoromethyl, aryl, aryloxy, heteroaryl; or wherein $R^3$ is $-SR_e$; wherein $R_e$ is hydrogen, $(C_1-C_{10})$alkyl, $(C_3-C_8)$cycloalkyl, aryl, benzyl, phenethyl, or heteroaryl; and further wherein any aryl, aryloxy, heteroaryl, benzyl, or phenethyl may optionally be substituted with 1, 2, or 3 substituents selected from the group consisting of halo, nitro, cyano, hydroxy, $(C_1-C_{10})$alkyl, $(C_3-C_8)$cycloalkyl, $(C_1-C_{10})$alkoxy, $(C_1-C_{10})$alkanoyl, $(C_2-C_{10})$alkanoyloxy, and trifluoromethyl; or a pharmaceutically acceptable salt thereof.

A preferred compound is a compound of formula I wherein: $R^1$ and $R^2$ are each independently hydrogen, carboxy, $(C_1-C_{10})$alkyl, $(C_3-C_8)$cycloalkyl, $(C_2-C_{10})$alkenyl, $(C_2-C_{10})$alkynyl, $-COOR_a$, $-CONR_bR_c$, cyano, $-C(=O)R_d$, $-OR_c$, aryl, heteroaryl, oxazolidinyl, isoxazolidinyl, morpholinyl, $-S(O)_mR_f$, $-NR_gR_h$, azido, or halo; $R^3$ is $(C_1-C_{10})$alkyl, $(C_2-C_{10})$alkenyl, $(C_2-C_{10})$alkynyl, $(C_1-C_{10})$alkanoyl, $(C_3-C^8)$cycloalkyl, aryl, heteroaryl, aryl$(C_1-C_{10})$alkyl, heteroaryl$(C_1-C_{10})$alkyl, or $-CH_2R_i$, wherein $R_i$ is halo, cyano, cyanato, $-OR_j$, $-NR_kR_l$, azido, $-SR_m$, or $(C_3-C_8)$cycloalkyl; $R^4$ is hydrogen, $(C_1-C_{10})$alkyl, $(C_3-C_8)$cycloalkyl, $(C_2-C_{10})$alkenyl, $(C_2-C_{10})$alkynyl, aryl, or heteroaryl; m and n are each independently 0, 1, or 2; each $R_a-R_f$ is independently hydrogen, $(C_1-C_{10})$alkyl, $(C_3-C_8)$cycloalkyl, $(C_2-C_{10})$alkenyl, $(C_2-C_{10})$alkynyl, aryl, or heteroaryl; each $R_g$ or $R_h$ is independently hydrogen, $(C_1-C_{10})$alkyl, $(C_3-C_8)$cycloalkyl, $(C_2-C_{10})$alkenyl, $(C_2-C_{10})$alkynyl, $(C_1-C_{10})$alkanoyl, aryl, benzyl, phenethyl, heteroaryl oxazolidinyl, isoxazolidinyl, or morpholinyl; or $R_g$ and $R_h$ together with the nitrogen to which they are attached are triazolyl, imidazolyl, oxazolidinyl, isoxazolidinyl, pyrrolyl, morpholino, piperidino, pyrrolidino, pyrazolyl, indolyl, or tetrazolyl; $R_j$ is hydrogen, $(C_1-C_{10})$alkyl, $(C_3-C_8)$cycloalkyl, $(C_2-C_{10})$alkenyl, $(C_2-C_{10})$alkynyl, $-C(=O)N(R_p)_2$, aryl, heteroaryl, arylcarbonyl, heteroarylcarbonyl, or $(C_1-C_{10})$alkanoyl, wherein each $R_p$ is independently hydrogen, $(C_1-C_{10})$alkyl, aryl, benzyl, phenethyl, or heteroaryl; each $R_k$ or $R_l$ is independently hydrogen, $(C_1-C_{10})$alkyl, $(C_3-C_8)$cycloalkyl, $(C_2-C_{10})$alkenyl, $(C_2-C_{10})$alkynyl, $(C_1-C_{10})$alkanoyl, $-C(=O)N(R_q)_2$, aryl, benzyl, phenethyl, heteroaryl oxazolidinyl, isoxazolidinyl, or morpholinyl, wherein each $R_q$ is independently hydrogen, $(C_1-C_{10})$alkyl, aryl, benzyl, phenethyl, or heteroaryl; or $R_k$ and $R_l$ together with the nitrogen to which they are attached are triazolyl, imidazolyl, oxazolidinyl, isoxazolidinyl, pyrrolyl, morpholino, piperidino, pyrrolidino, pyrazolyl, indolyl, or tetrazolyl; and $R_m$ is hydrogen, $(C_1-C_{10})$alkyl, $(C_3-C_8)$cycloalkyl, $(C_2-C_{10})$alkenyl, $(C_2-C_{10})$alkynyl, $(C_1-C_{10})$alkanoyl, aryl, benzyl, phenethyl, heteroaryl, oxazolidinyl, isoxazolidinyl, or morpholinyl; wherein any $(C_1-C_{10})$alkyl, $(C_3-C_8)$cycloalkyl, $(C_2-C_{10})$alkenyl, $(C_2-C_{10})$alkynyl, $(C_1-C_{10})$alkanoyl, aryl, benzyl, phenethyl, heteroaryl, arylcarbonyl, heteroarylcarbonyl, oxazolidinyl, isoxazolidinyl, or morpholinyl of $R^1-R^4$, $R_a-R_m$, or $R_p-R_q$, may optionally be substituted with 1, 2, or 3 Z; and each Z is independently halo, nitro, cyano, hydroxy, $(C_1-C_{10})$alkyl, $(C_3-C_8)$cycloalkyl, $(C_1-C_{10})$alkoxy, $(C_1-C_{10})$alkanoyl, $(C_2-C_{10})$alkanoyloxy, trifluoromethyl, aryl, aryloxy, heteroaryl, or $-SR_n$, wherein $R_n$ is hydrogen, $(C_1-C_{10})$alkyl, $(C_3-C_8)$cycloalkyl, aryl, benzyl, phenethyl, or heteroaryl; and wherein any aryl, aryloxy, heteroaryl, benzyl, or phenethyl of Z may optionally be substituted with 1, 2, or 3 substituents selected from the group consisting of halo, nitro, cyano, hydroxy, $(C_1-C_{10})$alkyl, $(C_3-C_8)$cycloalkyl, $(C_1-C_{10})$ alkoxy, $(C_1-C_{10})$alkanoyl, $(C_2-C_{10})$alkanoyloxy, and trifluoromethyl; or a pharmaceutically acceptable salt thereof.

Another preferred compound is a compound of formula (1) wherein: $R^1$ is hydrogen; $R^2$ is $(C_1-C_{10})$alkyl, $-COOR_a$, $-CONR_bR_c$, cyano, $-C(=O)R_d$, $-OR_e$, aryl, heteroaryl, oxazolidinyl, isoxazolidinyl, morpholinyl, $-S(O)_mR_f$, $-NR_gR_h$, azido, or halo; $R^3$ is $(C_2-C_{10})$alkenyl, $(C_2-C_{10})$alkynyl, $(C_1-C_{10})$alkanoyl, or $-CH_2R_i$, wherein $R_i$ is halo, cyano, cyanato, 13 $OR_j$, $-NR_kR_l$, azido, $-SR_m$, or $(C_3-C_8)$cycloalkyl; $R^4$ is hydrogen, $(C_1-C_{10})$alkyl, $(C_3-C_8)$cycloalkyl, $(C_2-C_{10})$alkenyl, $(C_2-C_{10})$alkynyl, aryl, or heteroaryl; m and n are each independently 0, 1, or 2; each $R_a-R_f$ is independently hydrogen, $(C_1-C_{10})$alkyl, $(C_3-C_8)$cycloalkyl, $(C_2-C_{10})$alkenyl, $(C_2-C_{10})$alkynyl, aryl, or heteroaryl; each $R_g$ or $R_h$ is independently hydrogen, $(C_1-C_{10})$alkyl, $(C_3-C_8)$cycloalkyl, $(C_2-C_{10})$alkenyl, $(C_2-C_{10})$alkynyl, $(C_1-C_{10})$alkanoyl, aryl, benzyl, phenethyl, or or $R_g$ and $R_h$ together with the nitrogen to which they are attached are morpholino, piperidino, or pyrrolidino; $R_j$ is hydrogen, $(C_1-C_{10})$alkyl, $(C_3-C_8)$cycloalkyl, $(C_2-C_{10})$alkenyl, $(C_2-C_{10})$alkynyl, $-C(=O)N(R_p)_2$, aryl, heteroaryl, arylcarbonyl, heteroarylcarbonyl, or $(C_1-C_{10})$alkanoyl, wherein each $R_p$ is independently hydrogen, $(C_1-C_{10})$alkyl, aryl, benzyl, phenethyl, or heteroaryl; each $R_k$ or $R_l$ is independently hydrogen, $(C_1-C_{10})$alkyl, $(C_1-C_{10})$alkanoyl, aryl, benzyl, or phenethyl; or $R_k$ and $R_l$ together with the nitrogen to which they are attached are morpholino, piperidino, or pyrrolidino; and $R_m$ is hydrogen, $(C_1-C_{10})$alkyl, $(C_3-C_8)$cycloalkyl, $(C_2-C_{10})$alkenyl, or $(C_2-C_{10})$alkynyl; wherein any $(C_1-C_{10})$alkyl, $(C_1-C_{10})$alkanoyl, aryl, benzyl, phenethyl, heteroaryl, arylcarbonyl, or heteroarylcarbonyl of $R^1-R^4$, $R_a-R_m$, or $R_p$, may optionally be substituted with 1, 2, or 3 Z; and each Z is independently halo, nitro, cyano, hydroxy, $(C_1-C_{10})$alkyl, $(C_1-C_{10})$alkoxy, $(C_1-C_{10})$alkanoyl, $(C_2-C_{10})$alkanoyloxy, trifluoromethyl, aryl, aryloxy, heteroaryl, or $-SR_n$, wherein $R_n$ is hydrogen, $(C_1-C_{10})$alkyl, $(C_3-C_8)$cycloalkyl, aryl, benzyl, phenethyl, or heteroaryl; and further wherein any aryl, aryloxy, heteroaryl, benzyl, or phenethyl of Z may optionally be substituted with 1, 2, or 3 substituents selected from the group consisting of halo, nitro, cyano, hydroxy, $(C_1-C_{10})$alkyl, $(C_1-C_{10})$alkoxy, $(C_1-C_{10})$alkanoyl, $(C_2-C_{10})$alkanoyloxy, and trifluoromethyl; or a pharmaceutically acceptable salt thereof.

Processes and novel intermediates useful for preparing compounds of formula I are provided as further embodiments of the invention and are illustrated by the following procedures in which the meanings of the generic radicals are as given above unless otherwise qualified. Certain compounds of formula (I) are also useful as intermediates for preparing other compounds of formula (I).

A compound of formula I wherein n is 1 can be prepared by oxidation of suitably protected intermediates wherein n is 0, using one equivalent of an acceptable oxidizing agent, for example, mCPBA. For example, oxidation of compound 7 (FIG. 1) or compound 19 (FIG. 4) would produce selective oxidation of the thiazolidine sulfur, thus leading to intermediates suitable for the preparation of compounds of formula I (n=1).

A compound of formula I wherein $R^4$ is hydrogen can generally be prepared from a corresponding ester of formula I wherein $R^4$ is other than hydrogen by hydrolysis, using techniques which are well known in the art, as illustrated in FIG. 1 for the conversion of a compound of formula 8 to a compound of formula 9.

It is noted that many of the starting materials employed in the synthetic methods described above are commercially available or are reported in the scientific literature. It is also noted that it may be desirable to optionally use a protecting group during all or portions of the above described synthetic procedures. Such protecting groups and methods for their introduction and removal are well known in the art (see Greene, T. W.; Wutz, P. G. M. "Protecting Groups In Organic Synthesis" second edition, 1991, New York, John Wiley & sons, Inc.).

Compounds of Formula I can be prepared as illustrated in FIGS. 1, 2, 4, and 5. Thus, as shown in FIG. 1, the commercially available 6-APA (1), was converted into 6,6-dibromopenicillanic acid by employing the method of R. A. Volkmann, et. al. (J. Org. Chem., 47, 3344–5 (1982)). Esterification with diphenyldiazomethane produced ester 3. Treatment of dibromide 3 with tert-butylmagnesium chloride, followed by a solution of anhydrous formaldehyde produced a diastereomeric mixture of bromoalcohols 4. Bromides 4 could be stereoselectively reduced to 6β-(hydroxymethyl)penicillinate 5 upon treatment with tributyltin hydride in the presence of either of the radical initiators AIBN or 1,1'-azobis(cyclohexanecarbonitrile). The corresponding mesylate 6 could be obtained by treatment of 5 with methanesulfonyl chloride in the presence of dimethylaminopyridine (DMAP). Thioacetate 7 could be prepared from 6 upon treatment with a solution of cesium thioacetate. Methoxide cleavage of thioester 7, yielded thiol 8 which was further deprotected to produce acid 9.

Figure 2:
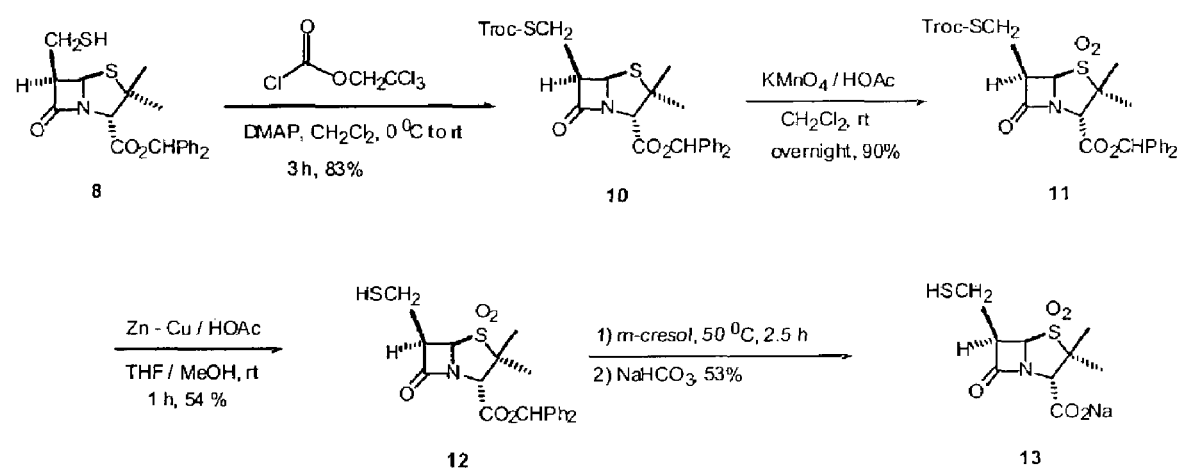
FIG. 2 illustrates the preparation of compounds of the invention.

As shown in FIG. 2, thiol 8 can be protected as the trichloroethylthiocarbonate 10 by treatment with trichloroethylchloroformate. Oxidation of the sulfur of this protected compound then produced the corresponding sulfone 11. Removal of the Troc protecting group (2',2',2' trichloroethoxycarbonyl' "Troc") by treatment with zinc-copper couple produced mercaptan 12, which was further deprotected to produce carboxylate 13.

Figure 4:
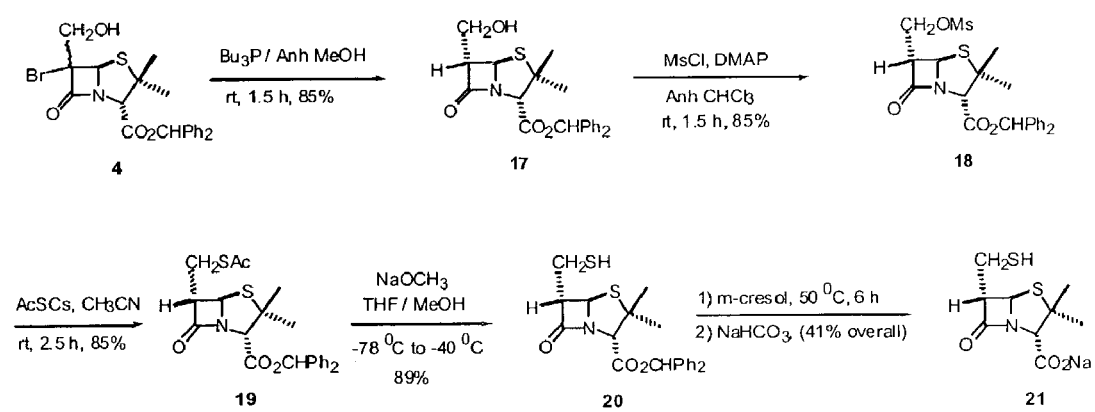
FIG. 4 illustrates the preparation of compounds of the invention.

As shown in FIG. 4, treatment of bromoalcohols 4 with tributylphosphine produced the 6α-hydroxymethylpenicillinate 17, which was converted to mesylate 18 and treated with cesium thioacetate to generate thioester 19. Methanolysis of the thioester by treatment with sodium methoxide produced mercaptan 20. Further deprotection of the benzhydryl ester by heating with m-cresol produced the fully deprotected 21.

Figure 5:
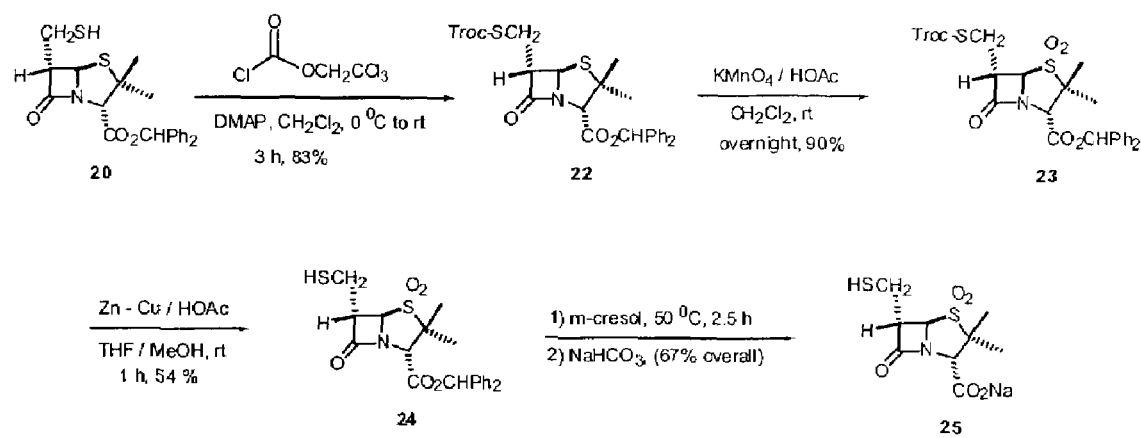
FIG. 5 illustrates the preparation of compounds of the invention.

FIG. 5 illustrates the procedure utilized for the preparation of the corresponding sulfone, 25. Thus 6α-(mercaptomethyl)penicillinate 20 was selectively protected by reaction with trichloroethyl chloroformate and oxidized with potassium permanganate to produce sulfone 23. Removal of the Troc group by treatment with zinc-copper couple produced mercaptan 24. The benzhydryl ester was subsequently removed to generate carboxylate 25.

Figure 3:
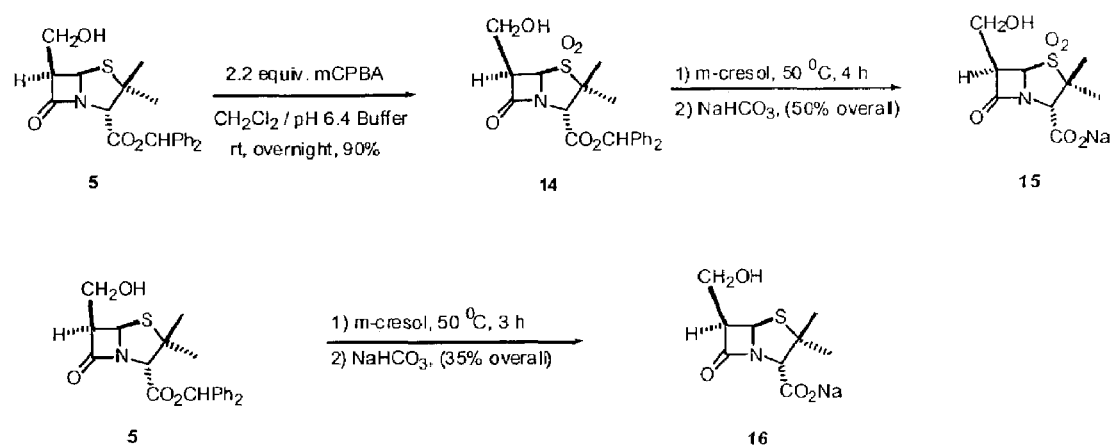
FIG. 3 illustrates the preparation of known alcoholic β-lactamase inhibitors (15 and 16), which were generated for comparison purposes.
Figure 6:
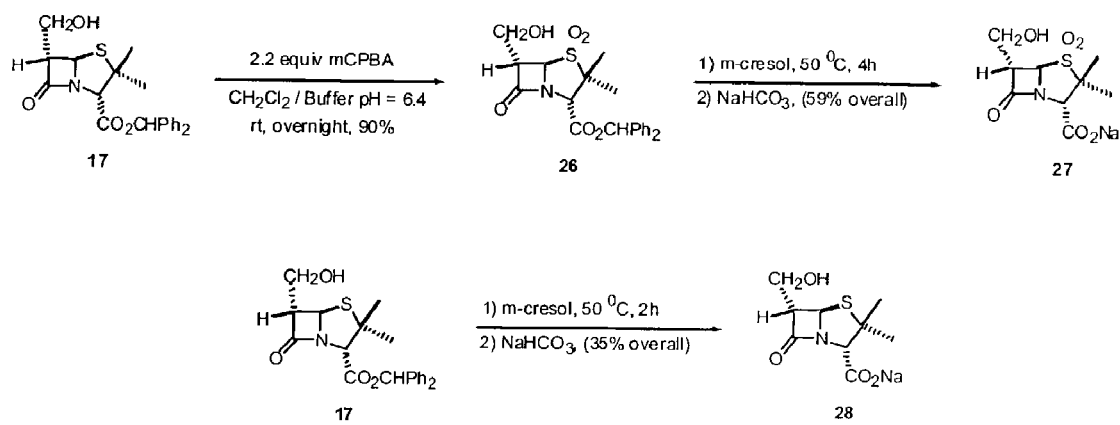
FIG. 6 illustrates the preparation of known alcoholic β-lactamase inhibitors (27 and 28), which were generated for comparison purposes.

FIG. 3 and FIG. 6 illustrate the preparation of the analogous 6α- and 6β-(hydroxymethyl)penicillinates, which were prepared for comparison purposes. These were prepared according to the procedure reported by Mobashery (Miyashita, K.; Massova, I.; Taibi, P.; Mobashery, S. J. Am. Chem. Soc. 117, 11055–11059 (1995)), which is itself a variation of an earlier procedure reported by DiNinno (DiNinno, F.; Beattie, T. R.; Christensen, B. G. J. Org. Chem. 42, 2960 (1977)).

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example, calcium) salts of carboxylic acids can also be made.

Preferred salts of the invention include disalts prepared from acids of formula (I) wherein $R^2$ is carboxy, and $R^4$ is hydrogen, or wherein $R^1$ is $(C_1-C_{10})$alkanoyl or alkoxycarbonyl. Preferred salts also include monosalts (e.g. a sodium salt) prepared from an acid of formula (I) wherein $R^4$ is hydrogen. The invention also provides a method for preparing a compound of the invention comprising forming a mono-, di-, or tri-salt from a corresponding compound of formula (I).

The compounds of formula I can be formulated as pharmaceutical compositions and administered to a mammalian host, such as a human patient in a variety of forms adapted to a selected route of administration, i.e., by oral, parenteral, intravenous, intramuscular, topical, or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred nethods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are disclosed in Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%. Single dosages for injection, infusion or ingestion will generally vary between 50–1500 mg, and may be administered, i.e., 1–3 times daily, to yield levels of about 0.5–50 mg/kg, for adults.

Accordingly, the invention provides a pharmaceutical composition, comprising an effective amount of a compound of formula I as described hereinabove; or a pharmaceutically acceptable salt thereof, and a pharmaceutically acceptable carrier. The invention also provides a pharmaceutical composition comprising an effective amount of a compound of formula I, as described hereinabove, or a pharmaceutically acceptable salt thereof, in combination with a β-lactam antibiotic (e.g., a penicillin, cephalosporin, carbapenem, oxacephem, monobactum, or penem) and a pharmaceutically acceptable carrier. Any β-Lactam antibiotic is suitable for use in the pharmaceutical composition of the invention. β-Lactam antibiotics which are well known in the art include those disclosed by R. B. Morin and M. Gorin, M. Eds.; Academic Press, New York, 1982; vol. 1–3. Preferred β-Lactam antibiotics, suitable for use in the pharmaceutical composition of the invention, include β-lactam antibiotics which are preferentially deactivated by Class A and Class C β-lactamase enzymes, for example, amoxicillin, piperacillin, ampicillin, ceftizoxime, cefotaxime, cefuroxime, cephalexin, cefaclor, cephaloridine, and ceftazidime. The ability of a compound of the invention to function as a β-lactamase inhibitor can be demonstrated using the test described below, or using other tests which are well known in the art.

Representative compounds of the invention were evaluated as inhibitors of two serine β-lactamases: *Enterobacter cloacae* P99 (class C), TEM-1 (class A), as well as two class B enzymes: the L1 metallo-β-lactamse derived from *Stenotrophomonas maltophilia*) and the metallo-β-lactamase derived from the *Bacillus cereus* microorganism. The $IC_{50}$ value of each compound was determined as follows.

Assay method involves 4 min incubation of a solution of inhibitor and enzyme (0.1 to 1 µM in enzyme), followed by transfer of an aliquot into a dilute solution of the substrate nitrocefin. Hydrolysis is monitored spectrophotometrically at 480 nm for 1 min. The rate is constant throughout this period. Error is ±10%, based on multiple experiments.

The results are summarized in Table 1. The relative inhibition activity of both the serine and metallo-β-lactamases by compounds 13, 9, 21, and 25 of the invention is contrasted with that of previously reported compounds 15, 16, 27, and 28. In particular, all of the former 6-(mercaptomethyl)pencillinate of this invention possess the ability to inhibit the class B β-lactamases, while none of the latter, previously known, 6-(hydroxymethyl)penicillinates possess such ability. Compound 13, in particular, possesses excellent broad spectrum inhibitory activity.

TABLE 1

Inhibition of Serine and Metallo-β-lactamases (IC$_{50}$, µM)

| Compound | TEM-1 (Class A) (Serine) | P99 (Class C) (Serine) | L1 (Class B) (Metallo) | BC1 (Class B) (Metallo) |
|---|---|---|---|---|
| Tazobactam | 0.122 | 53.2 | >2000 | >2000 |
| 16 | 752 | 409 | >2000 | >2000 |
| 9 | 601 | 0.10 | 72.2 | 12.3 |
| 15 | 0.65 | 3.9 | >2000 | >2000 |
| 13 | 6.8 | 10.5 | 0.13 | 64 |
| 28 | 275 | 96.2 | >2000 | >2000 |
| 21 | 648 | 3.75 | 81.4 | 7.6 |
| 27 | 14.6 | 10.0 | >2000 | >2000 |
| 25 | 51.7 | 7.5 | 0.82 | 770 |

Compounds of the invention have been shown to possess activity as inhibitors of both the serine and metallo-β-lactamases. Accordingly, the invention provides a method comprising inhibiting both serine and/or metallo-β-lactamases by contacting said enzymes with an effective amount of a compound of formula I; or a pharmaceutically acceptable salt thereof. The β-lactamases may be contacted with the compound of claim 1 in vitro or in vivo. The invention also provides a therapeutic method comprising inhibiting either or both serine and metallo-β-lactamases in a mammal (preferably a human) in need of such therapy, by administering an effective inhibitory amount of a compound of formula I; or a pharmaceutically acceptable salt thereof.

Because compounds of the invention inhibit both the serine and metallo-β-lactamase enzymes, they may also be useful to increase the effectiveness of β-lactam antibiotics which are degraded by such enzymes. Thus these compounds should have utility in the treatment of infections caused by bacteria containing either serine or metallo-β lactamases, thereby allowing the antibiotic to reach its target in the bacerial cell wall. Accordingly, the invention provides a method comprising enhancing (increasing by a detectable amount) the activity of a β-lactam antibiotic, by administering the β-lactam antibiotic to a mammal (preferably a human) in need thereof, in combination with an effective amount of a compound of formula I; or a pharmaceutically acceptable salt thereof.

The invention also provides a method comprising treating a β-lactam resistant bacterial infection in a mammal (preferably a human), by administering an effective amount of a β-lactam antibiotic in combination with an effective serine or metallo-β-lactamase inhibiting amount of a compound of formula I; or a pharmaceutically acceptable salt thereof.

Additionally, the invention provides a compound of formula I for use in medical therapy (preferably for use in treating a β-lactam resistant infection), as well as the use of a compound of formula I for the manufacture of a medicament useful for reducing both serine and metallo-β-lactamase activity in a mammal.

The invention will now be illustrated by the following non-limiting examples.

EXAMPLE 1

Sodium Salt of 6β-(mercaptomethyl)penicillanic acid (9)

(a) 6,6-Dibromopenicillanic acid (2). To a 3L three necked, round bottomed flask equipped with an overhead mechanical stirrer and thermometer was added dichloromethane (1,500 mL) and the contents cooled to approximately 5° C. To the solvent was then added $Br_2$ (359.7 g, 115.5 mL, 2.25 mol), $H_2SO_4$ (2.5 N, 600 mL, 1.5 mol), and $NaNO_2$ (103.5 g, 1.5 mol). Some foaming was observed after the addition of the $NaNO_2$. 6-APA (1,162 g, 0.75 mol) was then added portionwise over a period of 30 min while maintaining the reaction temperature between 4 to 10° C. The resultant dark red solution was stirred at 5° C. for 30 min. A solution of aqueous $NaHSO_3$ (1 M, 1,230 mL) was added dropwise at 5 to 15° C. over a period of 20 min until the bromine color was gone, forming a light yellow solution. The organic layer was separated and the aqueous layer extracted with additional dichloromethane (2×400 mL). The combined organic extracts were washed with brine (2×600 mL), dried over $Na_2SO_4$, and concentrated to give 229 g of crude product (crude yield=85%). This material was utilized in the following reactions without further purification. $^1H$ NMR ($CDCl_3$) δ=5.78 (1H, s, C5 CH), 4.58 (1H, s, C3 CH), 1.65 (3H, s, Me), 1.56 (3H, s, Me).

(b) Benzhydryl 6,6-dibromopenicillinate (3). To a solution of 6,6-dibromopenicillanic acid, 2, (420 g, 1.17 mol) in acetone (2 L) at 0° C. was added a solution of diphenyldiazomethane (250 g, 1.23 mol) in acetone (500 mL), and the resultant mixture was mechanically stirred for 20 h at room temperature. The solvent was then removed in vacuo and the resultant residue was purified by flash chromatography on silica gel (15% $CH_2Cl_2$/hexane) to produce pure 3 (90% yield). $^1H$ NMR ($CDCl_3$) δ=7.36 (10H, m, Ar), 6.95 (1H, s, $CHPh_2$), 5.84 (1H, s, C5 CH), 4.63 (1H, s, C3 CH), 1.62 (1H, s, Me), 1.28 (1H, s, Me).

(c) Benzhydryl 6-bromo-6-hydroxymethylpenicillinate (4). To a cold (−78 ° C.) solution of benzhydryl 6,6-dibromopenicillinate 3 (31.5 g, 60 mmol) in anh THF (150 mL) was added t-butylmagnesium chloride (1M, 60 mL, 60 mmol) slowly while maintaining an argon atmosphere over the reaction. The reaction mixture was stirred at −78° C. for 45 min and then a cold solution of anhydrous formaldehyde (prepared according to the method of Schlosser, et. al. Synlett 704 (1990)) in THF (0.4 M, 300 mL) was added slowly. Stirring was continued for 1 h at −78° C., then the reaction was slowly warmed to rt. The reaction mixture was then quenched by the addition of glacial acetic acid (4.0 mL) and $CH_2Cl_2$ (500 mL) was added. The organic layer was then washed with water (3×1L), brine (1×1L), dried over $Na_2SO_4$ and concentrated to produce crude product. The resultant material was further purified by flash chromatography on silica gel (3% $EtOAc/CH_2Cl_2$) to produce 10.5 g (36%) 4 as a mixture of diastereomers. α-bromo-β-methylalcohol (4a): $^1H$ NMR ($CDCl_3$) δ=7.31 (10H, m, Ar), 6.93 (1H, s, $CHPh_2$), 5.56 (1H, s, C5 CH), 4.61 (1H, s, C3 CH), 4.08–4.21 (2H, m, $CH_2$), 1.65 (3H, s, Me), 1.27 (3H, s, Me). β-bromo-α-methylalcohol (4b) $^1H$ NMR ($CDCl_3$) δ=7.33 (10H, m, Ar), 6.93 (1H, s, $CHPh_2$), 5.66 (1H, s, C5 CH), 4.58 (1H, s, C3 CH), 4.03–4.25 (2H, m, $CH_2$), 162 (3H, s, Me), 1.28 (3H, s, Me). Formaldehyde solution: Paraformaldehyde (dried overnight at high vacuum over $P_2O_5$) and p-toluenesulfonic anhydride (4.9 g, 15 mmol) were placed in a dry three necked flask and anh THF (1000 mL) was added. The mixturee was heated and a slow distillation of solvent was maintained. Under a weak stream of argon passing through the vessel, a solution of anhydrous monomeric formaldehyde in THF was collected in a dry flask maintained at or below 0° C. The concentration of formaldehyde in the THF was ascertained by 1H NMR (δ=9.70, s) and the resultant solution was stored at −78° C. Typically, the concentration was found to be in the 0.4 to 0.6 M range.

(d) Benzhydryl 6β-(hydroxymethyl)penicillinate (5). To a solution of the diastereomeric mixture 4 (2.0 g, 4.2 mmol) in dry $CH_2Cl_2$ (25 mL) under argon were added tributyltin hydride (1.22 g, 1.13 mL, 4.2 mmol) and 1,1'-azobis (cyclohexanecarbonitrile) (20 mg, 0.08 mmol). The resultant solution was refluxed for 2 h and then evaporated in vacuo to dryness. The oily residue was further purified by flash chromatography on silica gel (6% $EtOAc/CH_2Cl_2$) to produce 1.5 g (89%) of pure product. $^1H$ NMR ($CDCl_3$) δ=7.28–7.36 (10H, m, Ar), 6.94 (1H, s, $CHPh_2$), 5.50 (1H, d, J=4Hz, C5 CH), 4.52 (1H, s, C3 CH), 4.03–4.08 (2H, m, $CH_2$), 3.84–3.88 (1H, m, C6 CH), 1.64 (3H, s, Me), 1.28 (3H, s, Me).

(e) Benzhydryl 6β-[(methanesulfonyloxy)methyl]penicillinate (6). To a solution of 5 (1.13 g, 2.84 mmol) in anh $CHCl_3$ (20 mL) under Ar were added 4-(dimethylamino) pyridine (0.35 g, 2.84 mmol) and methanesulfonyl chloride (0.36 g, 0.24 mL, 3.12 mmol). The mixture was stirred for 3 h at rt while monitoring the reaction by tlc. The reaction mixture was then washed with water (50 mL), brine (30 mL), and dried over $Na_2SO_4$. Concentration in vacuo, followed by flash chromatography (6% $EtOAc/CH_2Cl_2$) on silica gel produced 1.0 g (74%) pure product. $^1H$ NMR ($CDCl_3$) δ=7.30–7.38 (10H, m, Ar), 6.94 (1H, s, $CHPh_2$), 5.53 (1H, d, J=4.0 Hz), 4.49–4.68 (2H, m, $CH_2OMs$), 4.52 (1H, s, C3 CH), 4.04–4.09 (1H, m, C6 CH), 3.06 (3H, s, $OSO_2Me$), 1.63 (3H, s, Me), 1.28 (3H, s, Me).

(f) Benzhydryl 6β-(acetylsulfanylmethyl)penicillinate (7). To a solution of cesium thioacetate (generated by the method of Strijtveen et. al. J. Org. Chem. 51 3664–3671 (1986)), (1M, 2.1 mL, 2.1 mmol) in anh MeCN (10 mL) was added mesylate 6 (1.0 g, 2.1 mmol). The reaction mixture was stirred at rt overnight. The mixture was then concentrated under reduced pressure and the residue was poured into water (30 mL) and extracted with $CH_2Cl_2$ (2×30 mL). The combined organic layers were washed with water (2×40 mL), dried over $Na_2SO_4$, concentrated, and purified by flash chromatography on silica gel to produce 0.7 g (73%) of pure product. $^1H$ NMR ($CDCl_3$) δ=7.30–7.36 (10H, m, Ar), 6.94 (1H, s, $CHPh_2$), 5.43 (1H, d, J=4.0 Hz, C5 CH), 4.50 (1H, s, C3 CH), 3.80–3.86 (1H, m, C6 CH), 3.11–3.38 (2H, m, $CH_2$), 2.35 (3H, s, COMe), 1.62 (3H, s, Me), 1.26 (3H, s, Me).

(g) Benzhydryl 6β-(mercaptomethyl)penicillinate (8). To a solution of thioacetate 7 (0.55 g, 1.21 mmol) in a mixture of dry THF (6 mL) and dry MeOH (10 mL) at −78° C. was added a solution of $NaOCH_3$ in anhydrous MEOH (0.5 M, 2.66 mL, 1.33 mmol) dropwise over the course of 1 h. After the addition was complete, the reaction mixture was warmed to −40° C. and stirred for an additional 6 h at this temperature. $CH_2Cl_2$ was then added and the resultant solution was washed with cold 10% HCl, water, and brine. The organic layer was dried over $Na_2SO_4$, concentrated, and purified by flash chromatography on silica gel ($CH_2Cl_2$ as eluent) to produce 4.25 g (85%) of an 85:15 mixture of of the β and α isomer, respectively. β-isomer: $^1H$ NMR ($CDCl_3$) β=7.29–7.36 (10H, m, Ar), 6.94 (1H, s, $CHPh_2$), 5.49 (1H, d, J=4Hz, C5 CH), 4.49 (1H, s, C3 CH), 3.74–3.79 (1H, m, C6 CH), 2.82–2.98 (2H, m, $CH_2$), 1.62 (3H, s, Me), 1.27 (3H, s, Me). $^{13}C$ NMR ($CDCl_3$) δ=173.5, 167.3, 139.6, 139.5, 129.1, 129.0, 128.8, 128.6, 128.0, 127.4, 78.7, 69.4, 66.9, 64.6, 57.8, 32.8, 26.8, 21.2. IR (neat) 2567.7, 1774, 1740.5 cm-1. HRMS FAB (M+Li)$^+$ calcd for $C_{22}H_{23}LiNO_3S_2$, 420.1279; found 420.1263.

(h) Sodium Salt of 6β-(mercaptomethyl)penicillanic acid (9). A solution of benzhydryl ester 8 (82 mg, 0.20 mmol) in m-cresol (0.7 mL) was heated at 50° C. for 6 h under an argon atmosphere. The solution was then cooled to rt, diluted with ether, and treated with aqueous $NaHCO_3$ (17 mg, 0.2 mmol, in 4 mL deionized water). The separated aqueous layer was then purified on a column of CHP20P (Mitshubishi Chemical Corporation) using deionized water as eluent to produce 21 mg (39%) pure 9. $^1H$ NMR ($D_2O$) δ=5.28 (1H, d, J=4Hz, C5 CH), 3.97 (1H, s, C3 CH), 3.62–3.67 (1H, m, C6 CH), 2.59–2.77 (2H, m, $CH_2$), 1.45 (3H, s, Me), 1.35 (3H, s, Me).

Example 2

Sodium Salt of 6β-(mercaptomethyl)penicallin acid 1,1-dioxide (13).

(a) Benzhydryl 6β-(2',2',2'-trichloroethoxycarbonylsulfanylmethyl)penicillinate (10). To a solution of thiol 8 (0.85 g, 2.05 mmol) in dry $CH_2Cl_2$ (15 mL) at 0° C. under argon were added DMAP (0.25 g, 2.05 mmol) and 2,2,2-trichloroethyl chloroformate (0.52 g, 0.34 mL, 2.46 mmol). The reaction mixture was stirred at 0° C. for 1 h. Another 1.23 mmol of the 2,2,2-trichloroethyl chloroformate was then added. Stirring was continued at rt for 2 additional h. The solvent was removed under reduced pressure and the residue was purified by flash chromatography on silica gel ($CH_2Cl_2$ as eluent) to produce 1.0 g (83%) product, which remains an 85:15 mixture of the β and α isomers, respectively. $^1H$ NMR ($CDCl_3$) δ=7.31–7.40 (10H, m, Ar), 6.98 (1H, s, $CHPh_2$), 4.81–4.89 (2H, s, $CH_2CCl_3$), 4.65 (1H, d, J=4Hz, C5 CH), 4.56 (1H, s, C3 CH), 4.28–4.30 (1H, m, C6 CH), 3.45–3.69 (2, m, $CH_2S$), 1.56 (3H, s, Me), 1.11 (3H, s, Me).

(b) Benzhydryl 6β-(2',2',2'-trichloroethoxycarbonylsulfanylmethyl)-penicillinate 1,1-dioxide (11). To a solution of Troc-protected penicillinate 10 (1.00 g, 1.70 mmol) in $CH_2Cl_2$ (16 mL) were added acetic acid (2.5 mL) and $KMnO_4$ (0.64 g, 4.07 mmol). The mixture was stirred at rt overnight. The reaction mixture was then cooled in an ice bath and the excess $KMnO_4$ was destroyed with an aqueous solution of $NaHSO_3$. The organic layer was separated, washed with water and brine, dried over $Na_2SO_4$, and evaporated to dryness. The product was purified by flash chromatography ($CH_2Cl_2$ as eluent) to produce 0.62 g (59%) of β-isomer (11) and 0.25 g (24%) of the corresponding α-isomer. β-isomer (11): $^1H$ NMR ($CDCl_3$) δ=7.31–7.40 (10H, m, Ar), 6.98 (1H, s, $CHPh_2$), 4.89, 4.86, 4.84, 4.82 (2H, d of d, $CH_2CCl_3$), 4.65 (1H, d, J=4.0 Hz, C5 CH), 4.56 (1H, s, C3 CH), 4.28–4.30 (1H, m, C6 CH), 3.45–3.69 (2H, m, $CH_2S$), 1.56 (3H, s, Me), 1.11 (3H, s, Me). LRMS FAB (M+Li)$^+$ calcd for $C_{25}H_{24}Cl_3LiNO7S_2$: 626.0, found; 625.7.

(c) Benzhydryl 6'-(mercaptomethyl)penicillinate-1,1-dioxide (12). To a solution of Troc derivative 11 (0.621 g, 1.0 mmol) in a mixture of dry THF (8 mL) and dry MeOH (8 mL) were added acetic acid (4 mL) and zinc-copper couple (2.0 g). The reaction mixture was stirred at rt for 1 h. The mixture was then filtered through celite and evaporated to dryness. The residue was dissolved in $CH_2Cl_2$ (20 mL) and the resulting solution was washed with water and brine, dried over $Na_2SO_4$, and evaporated. Further purification by flash chromatography on silica gel ($CH_2Cl_2$ as eluent) produced 0.24 g (54%) pure product. $^1H$ NMR ($CDCl_3$) δ=7.32–7.39 (10H, m, Ar), 6.98 (1H, s, $CHPh_2$), 4.67–4.65 (1H, d, J=4 Hz, C5 CH), 4.54 (1H, s, C3 CH), 4.06–4.12 (1H, m, C6 CH), 3.00–3.37 (2H, m, $CH_2S$), 1.81-(1H, d of d, J=7.8 and 9.7 Hz, SH), 1.56 (3H, s, Me), 1.13 (3H, s, Me). $^{13}C$ NMR ($CDCl_3$) δ=173.3, 166.5, 139.2, 139.0, 129.24, 129.20, 129.1, 128.8, 128.2, 127.3, 127.2, 79.6, 65.0, 64.8, 63.4, 57.2, 20.1, 18.2, 17.9. IR(neat) 2571, 1794, 1755 cm-1. HRMS FAB (M+Li)$^+$ calcd for $C_{22}H_{23}LiNO_5S_2$: 452.1178; found 452.1196.

Example 3 Sodium Salt of 6β-(mercaptomethyl)penicallin acid 1,1-dioxide (13). A solution of benzhydryl ester 12 (70 mg, 0.16 mmol) in m-cresol (0.5 mL) was heated to 50° C. for 2.5 h. The reaction mixture was then cooled to rt, diluted with ether, treated with aqueous $NaHCO_3$ (15 mg in 4 mL deionized water). The aqueous layer was purified on a column of CHP20P (Mitsubishi Chemical Corporation) using deionized water as eluent to produce 25 mg (53%) of the final product. $^1H$ NMR ($D_2O$) δ=4.93 (1H, d, J=4.0 Hz, C5 CH), 4.13–4.17 (1H, m, C6 CH), 4.12 (1H, s, C3 CH), 2.83–3.03 (2H, m, $CH_2S$), 1.41 (3H, s, Me), 1.28 (3H, s, Me).

Example 3

Sodium Salt of 6β-(hydroxymethyl)penicillinate (16)

(a) Benzhydryl 6β-(hydroxymethyl)penicillinate-1,1-dioxide (14). To a solution of alcohol 5 (0.65 g, 1.63 mmol) in a two phase mixture of $CH_2Cl_2$ (10 mL) and pH=6.4 phosphate buffer (10 mL) was added mCPBA (0.88 g, 3.6 mmol). The mixture was stirred at rt overnight, and then diluted with additional $CH_2Cl_2$ (20 mL). the organic layer was washed with aqueous $NaHSO_3$, aqueous $NaHCO_3$, water, and brine. The organic layer was subsequently dried over $Na_2SO_4$, concentrated in vacuo, and purified by flash chromatography on silica gel (8% EtOAc/$CH_2Cl_2$ as eluent) to produce 0.63 g (90%) pure product. $^1H$ NMR (CDCl$_3$) δ=7.33–7.39 (10H, m, Ar), 6.99 (1H, s, CHPh$_2$), 4.66–4.67 (1H, d, C5 CH), 4.57 (1H, s, C3 CH), 4.11–4.35 (3H, m, C6 CH and CH$_2$O), 1.60 (3H, s, Me), 1.12 (3H, s, Me). LRMS FAB (M+Li)$^+$ calcd for C$_{22}$H$_{23}$LiNO$_6$S 436.1; found: 435.8.

(b) Sodium Salt of 6β-(hydroxymethyl)penicillinate-1,1-dioxide (15). A solution of ester 14 (0.1 g, 0.23 mmol) in cresol (0.9 mL) was heated at 50° C. for 4 h. The reaction mixture was then cooled to rt, diluted with ether, treated with aqueous NaHCO$_3$ (20 mg in 4 mL of deionized water, 0.23 mmol). The separated aqueous layer was then purified on a column of CHP20P (Mitsubishi Chemical Corporation) using deionized water as eluent to produce 33 mg (50%) pure compound. $^1$H NMR (D$_2$O) δ=4.97 (1H, d, J=4.0 Hz, C5 CH), 4.22 (1H, s, C3 CH), 3.96–4.23 (3H, m, C6 CH and CH$_2$O), 1.49 (3H, s, Me), 1.38 (3H, s, Me).

(c) Sodium Salt of 6β-(hydroxymethyl)penicillinate (16). Prepared from 5 by the same method as utilized in the case of 15, above (yield=35%). $^1$H NMR (D$_2$O) δ=5.39 (1H, d, J=4.0 Hz, C5 CH), 4.11 (1H, s, C3 CH), 3.57–3.86 (3H, m, C6 CH and CH$_2$O), 1.56 (3H, s, Me), 1.45 (3H, s, Me).

Example 4

Sodium Salt of 6α-(mercaptomethyl)penicillinate (21)

(a) Benzhydryl 6α-(hydroxymethyl)penicillinate (17). To a solution of bromoalcohol 4 (2.0 g, 4.2 mmol) in dry MeOH was added tributylphosphine (1.28 g, 1.56 mL, 6.3 mmol). The reaction mixture was then stirred for 1.5 h at rt. The mixture was concentrated under reduced pressure and the product purified by flash chromatography (7% EtOAc/CH$_2$Cl$_2$ as eluent) to produce an 85:15 mixture of α:β isomer respectively (85% yield). α-isomer: $^1$H NMR (CDCl$_3$) δ=7.29–7.36 (10H, m, Ar), 6.92 (1H, s, CHPh$_2$), 5.33 (1H, d, J=1.6 Hz, C5 CH), 4.58 (1H, s, C3 CH), 4.00–4.09 (2H, m, CH$_2$O), 3.51–3.53 (1H, m, C6 CH), 1.62 (3H, s, Me), 1.25 (3H, s, Me).

(b) Benzhydryl 6α-[(methanesulfonyloxy)methyl]penicillinate (18). Prepared from 17 by the same method as described for 6 above. It was possible to improve the isomeric ration of α:β to 95:5, respectively, due to the fact that the β-(hydroxymethylpenicillinate) reacted more slowly with mesyl chloride. α-isomer: $^1$H NMR (CDCl$_3$) δ=7.29–7.36 (10H, m, Ar), 6.93 (1H, s, CHPh$_2$), 5.35 (1H, d, J=1.2 Hz, C5 CH), 4.51–4.58 (3H, m, C3 CH and CH$_2$O), 3.66–3.69 (1H, m, C6 CH), 3.00 (3H, s, SO$_2$Me), 1.62 (3H, s, Me), 1.25 (3H, s, Me).

(c) Benzhydryl 6α-(acetylsulfanylmethyl)penicillinate (19). Prepared from 18 by the same method as described for 7 above (yield 85%). $^1$H NMR (CDCl$_3$) δ=7.28–7.36 (10H, m, Ar), 6.92 (1H, s, CHPh$_2$), 5.11 (1H, d, J=1.6Hz, C5 CH), 4.56 (1H, s, C3 CH), 3.50–3.54 (1H, m, C6 CH), 3.25–3.38 (2H, m, CH$_2$O), 2.34 (3H, s, SO$_2$Me), 1.59 (3H, s, Me), 1.23 (3H, s, Me).

(d) Benzhydryl 6α-(mercaptomethyl)penicillinate (20). Prepared from 19 by the same method as described for 8 above (yield 89%). $^1$H NMR (CDCl$_3$) δ=7.28–7.37 (10H, m, Ar), 6.93 (1H, s, CHPh$_2$), 5.23 (1H, d, J=1.2 Hz, C5 CH), 4.57 (1H, s, C3 CH), 3.53–3.56 (1H, m, C6 CH), 2.88–3.03 (2H, m, CH$_2$S), 1.61 (3H, s, Me), 1.25 (3H, s, Me). $^{13}$C NMR (CDCl$_3$) δ=172.2, 167.2, 139.65, 139.57, 129.02, 129.00, 128.76, 128.61, 127.94, 127.47, 78.71, 70.02, 66.06, 65.99, 64.22, 33.58, 26.35, 22.72. IR (neat) 2566.7 (SH), 1774.2, 1746.8 cm-1. HRMS (FAB), (M+Li)$^+$, calcd for C$_{22}$H$_{23}$LiNO$_3$S$_2$ 420.1279; found 420.1277.

(e) Sodium Salt of 6α-(mercaptomethyl)penicillinate (21). Prepared from 20 by the same method as described above for compound 9 (yield 41%). $^1$H NMR (D$_2$O) δ=5.04 (1H, d, J=1.4 Hz, C5 CH), 4.08 (1H, s, C3 CH), 3.34–3.38 (1H, m, C6 CH), 2.70–2.95 (2H, m, CH$_2$S), 1.45 (1H, s, Me), 1.34 (1H, s, Me).

Example 5

Sodium Salt of 6α-(mercaptomethyl)penicallin acid 1,1-dioxide (25)

(a) Benzhydryl 6α-(2',2',2'-trichloroethoxycarbonylsulfanylmethyl)-penicillinate (22). Prepared from 20 by the same procedure used in the preparation of compound 10 above (yield=69%). $^1$H NMR (CDCl$_3$) δ=7.29–7.36 (10H, m, Ar), 6.93 (1H, s, CHPh$_2$), 5.21 (1H, d, J=1.6 Hz), 4.87, 4.84, 4.83, 4.80 (2H, ABq, CH$_2$CCl$_3$), 4.57 (1H, s, C3 CH), 3.61–3.65 (1H, m, C6 CH), 3.28–3.46 (2H, m, CH$_2$S), 1.60 (3H, s, Me), 1.24 (3H, s, Me).

(b) Benzhydryl 6α-(2',2',2'-trichloroethoxycarbonylsulfanylmethyl)-penicillinate 1,1-dioxide (23). Prepared from 22 by the same method used in the preparation of compound 11 above (yield=90%). $^1$H NMR (CDCl$_3$) δ=7.29–7.36 (10H, m, Ar), 6.93 (1H, s, CHPh$_2$), 4.894, 4.865, 4.859, 4.829 (ABq, CH$_2$CCl$_3$), 4.55 (1H, d, J=1.9 Hz, C5 CH), 4.48 (1H, s, C3 CH), 4.01–4.03 (1H, m, C6 CH), 3.40–3.49 (2H, m, CH$_2$S), 1.57 (3H, s, Me), 1.11 (3H, s, Me). LRMS (FAB) (M+Li)$^+$ calcd for C$_{25}$H$_{24}$Cl$_3$LiNO7S$_2$: 626.0, found; 625.6.

(c) Benzhydryl 6α-(mercaptomethyl)penicillinate-1,1-dioxide 24. Prepared from 23 by the same method used in the preparation of compound 12 above (yield=77%). $^1$H NMR (CDCl$_3$) δ=7.30–7.39 (10H, m, Ar), 6.96 (1H, s, CHPh$_2$), 4.55 (1H, d, J=1.8 Hz, C5 CH), 4.49 (1H, s, C3 CH), 3.95–3.98 (1H, m, C6 CH), 3.01–3.05 (2H, m, CH$_2$S), 1.64–1.68 (1H, t, J=8.6 Hz, SH), 1.58 (3H, s, Me), 1.14 (3H, s, Me). $^{13}$C NMR (CDCl$_3$) δ=171.07, 166.22, 139.29, 139.10, 129.21, 129.11, 128.79, 128.01, 127.26, 79.55, 65.44, 63.65, 63.29, 55.50, 21.44, 20.18, 19.11. IR (neat) 2570 (SH), 1793, 1755 cm-1. HRMS (FAB) (M+Li)$^+$ calcd for calcd for C$_{22}$H$_{23}$LiNO$_5$S$_2$: 452.1178; found 452.1171.

(d) Sodium Salt of 6α-(mercaptomethyl)penicallin acid 1,1-dioxide (25). Prepared from 24 by the same method used in the preparation of compound 13 above (yield=67%). $^1$H NMR (D$_2$O) δ=5.12 (1H, s, C5 CH), 4.37 (1H, s, C3 CH), 3.76–3.81 (1H, m, C6 CH), 3.14–3.26 (2H, m, CH$_2$S), 1.72 (3H, s, Me), 1.19 (3H, s, Me).

Example 6

Sodium Salt of 6α-(hydroxymethyl)penicillinate (28)

(a) Benzhydryl 6α-(hydroxymethyl)penicillinate-1,1-dioxide (26). Prepared from 17 using the same method as described for the preparation of compound 14 above (yield=90%). $^1$H NMR (CDCl$_3$) δ=7.30–7.52 (10H, m, Ar), 6.96 (1H, s, CHPh$_2$), 4.66 (1H, d, J=1.8 Hz, C5 CH), 4.50 (1H, s, C3 CH), 3.98–4.18 (2H, m, CH$_2$O), 3.88–3.89 (1H, m, C6 CH), 1.57 (3H, s, Me), 1.13 (3H, s, Me). LRMS (FAB) (M+Li)$^+$ calcd for C$_{22}$H$_{23}$LiNO$_6$S 436.1; found: 435.8.

(b) Sodium Salt of 6α-(hydroxymethyl)penicillinate-1,1-dioxide (27). Prepared from 26 using the same method as described for the preparation of compound 15, above (yield=59%). $^1$H NMR (D$_2$O) δ=4.91 (1H, d, J=1.4 Hz, C5 CH), 4.17 (1H, s, C3 CH), 3.91–4.05 (2H, m, CH$_2$O), 3.80–3.85 (1H, m, C6 CH), 1.51 (3H, s, Me), 1.38 (3H, s, Me).

(c) Sodium Salt of 6α-(hydroxymethyl)penicillinate (28). Prepared from 17 using the same procedure as described for the preparation of 16 above (yield=35%). $^1$H NMR (D$_2$O) δ=5.17 (1H, d, J=1.4 Hz, C5 CH), 4.16 (1H, s, C3 CH), 3.82–3.89 (2H, m, CH$_2$O), 3.46 (1H, m, C6 CH), 1.53 (3H, s, Me), 1.41 (3H, s, Me).

Example 7

The following illustrate representative pharmaceutical dosage forms, containing a compound of formula I ('Compound X'), for therapeutic or prophylactic use in humans.

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0–7.5) | q.s. |
| Water for injection | q.s. ad 1 mL |

| (v) Injection 2 (10 mg/ml) | mg/ml |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0–7.5) | q.s. |
| Water for injection | q.s. ad 1 mL |

| (vi) Aerosol | mg/can |
|---|---|
| 'Compound X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

| (vii) Tablet | mg/tablet |
|---|---|
| 'Compound X' | 100.0 |
| β-lactam antibiotic | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 400.0 |

| (viii) Tablet | mg/tablet |
|---|---|
| 'Compound X' | 20.0 |
| β-lactam antibiotic | 10.0 |
| Microcrystalline cellulose | 410.0 |
| Starch | 50.0 |
| Sodium starch glycolate | 15.0 |
| Magnesium stearate | 5.0 |
| | 510.0 |

| (ix) Capsule | mg/capsule |
|---|---|
| 'Compound X' | 10.0 |
| β-lactam antibiotic | 10.0 |
| Colloidal silicon dioxide | 1.5 |
| Lactose | 465.5 |
| Pregelatinized starch | 120.0 |
| Magnesium stearate | 3.0 |
| | 610.0 |

| (x) Injection 1 (1 mg/ml) | mg/ml |
|---|---|
| 'Compound X' (free acid form) | 1.0 |
| β-lactam antibiotic | 1.0 |
| Dibasic sodium phosphate | 12.0 |

-continued

| (x) Injection 1 (1 mg/ml) | mg/ml |
|---|---|
| Monobasic sodium phosphate | 0.7 |
| Sodium chloride | 4.5 |
| 1.0 N Sodium hydroxide solution (pH adjustment to 7.0–7.5) | q.s. |
| Water for injection | q.s. ad 1 mL |

The above formulations may be obtained by conventional procedures well known in the pharmaceutical art. The β-lactam antibiotic in the above formulations can be any β-lactam antibiotic, including those identified specifically hereinabove.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula (I):

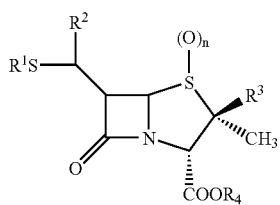

(I)

wherein $R^1$ and $R^2$ are H $R^3$ is hydrogen, carboxy, $(C_1–C_{10})$alkyl, $(C_2–C_{10})$alkenyl, $(C_2–C_{10})$alkynyl, $(C_1–C_{10})$alkanoyl, $(C_3–C_8)$cycloalkyl, aryl, heteroaryl, alkyl arylakyl, alkoxycarbonyl, oxazolinyl, isoazolidinyl, morpholinyl, heteroarylcarbonyl, alkanoyloxy, or alkoxy; or $—CH_2R_a$ wherein $R_a$ is halo, cyano, cyanato, $—OR_b$, $—NR_cR_d$, azido, $—SR_e$, $O—CO—R_f$, aryl, heteroaryl, $(C_3–C_8)$cycloalkyl, oxazolinyl, isoazolidinyl, morpholinyl, heteroarylcarbonyl, alkanoyloxy, or alkoxy;

$R^4$ is hydrogen, $(C_1–C_{10})$alkyl, $(C_3–C_8)$cycloalkyl, $(C_2–C_{10})$alkenyl, $(C_2–C_{10})$alkynyl, alkoxycarbonyl, aryl, heteroaryl, arylalkyl, oxazolinyl, isoazolidinyl, morpholinyl, heteroarylcarbonyl, or alkoxy;

n is 0, 1, or 2;

$R_b$ is hydrogen, $(C_1–C_{10})$alkyl, $(C_3–C_8)$cycloalkyl, $(C_2–C_{10})$alkenyl, $(C_2–C_{10})$alkynyl, $—C(=O)N(R_f)_2$, aryl, heteroaryl, arylcarbonyl, heteroarylcarbonyl, or $(C_1–C_{10})$alkanoyl, wherein each $R_f$ is independently hydrogen, $(C_1–C_{10})$alkyl, aryl, benzyl, phenethyl, or heteroaryl;

each $R_c$ or $R_d$ is independently hydrogen, $(C_1–C_{10})$alkyl, $(C_3–C_8)$cycloalkyl, $(C_2–C_{10})$alkenyl, $(C_2–C_{10})$alkynyl, $(C_1–C_{10})$alkanoyl, $—C(=O)N(R_f)_2$, aryl, benzyl, phenethyl, heteroaryl, oxazolidinyl, isoxazolidinyl, or morpholinyl, wherein each $R_f$ is independently hydrogen, $(C_1–C_{10})$alkyl, aryl, benzyl, phenethyl, or heteroaryl; or $R_c$ and $R_d$ together with the nitrogen to which they are attached are triazolyl, imidazolyl, oxazolidinyl, isoxazolidinyl, pyrrolyl, morpholino, piperidino, pyrrolidino, pyrazolyl, indolyl, or tetrazolyl; and $R_e$ is hydrogen, $(C_1–C_{10})$alkyl, $(C_3–C_8)$cycloalkyl, $(C_2–C_{10})$alkenyl, $(C_2–C_{10})$alkynyl, cyano, aryl, benzyl, phenethyl, heteroaryl, oxazolidinyl, isoxazolidinyl, or morpholinyl;

wherein any $(C_1–C_{10})$alkyl, $(C_3–C_8)$cycloalkyl, $(C_2–C_{10})$alkenyl, $(C_2–C_{10})$alkynyl, $(C_1–C_{10})$alkanoyl, aryl, benzyl, phenethyl, heteroaryl, arylcarbonyl, heteroarylcarbonyl, oxazolidinyl, isoxazolidinyl, or morpholinyl of $R^1–R^4$, $R_a–R_e$, or $R_f–R_g$, may optionally be substituted with 1, 2, or 3 Z; and each Z is independently halo, nitro, cyano, hydroxy, $(C_1–C_{10})$alkyl, $(C_3–C_8)$cycloalkyl, $(C_1–C_{10})$alkoxy, $(C_1–C_{10})$alkanoyl, $(C_2–C_{10})$alkanoyloxy, trifluoromethyl, aryl, aryloxy, or heteroaryl;

or a pharmaceutically acceptable salt thereof.

2. The compound of claim 1 wherein $R^1$ and $R^2$ are hydrogen, $R^3$ is methyl, ethyl, propyl, isopropyl, butyl, iso-butyl, sec-butyl, pentyl, 3-pentyl, hexyl, heptyl, octyl, nonyl, or decyl, and $R^4$ is hydrogen.

3. The compound of claim 1, wherein n is 2, $R^1$ and $R^2$ are hydrogen, $R^3$ is methyl, and $R^4$ is hydrogen.

4. A pharmaceutically acceptable salt of the compound of claim 3.

* * * * *